United States Patent
Li

(10) Patent No.: US 9,763,910 B1
(45) Date of Patent: Sep. 19, 2017

(54) COMBINATION THERAPY FOR TREATING CANCER

(71) Applicant: Shiming Li, Glastonbury, CT (US)

(72) Inventor: Shiming Li, Glastonbury, CT (US)

(73) Assignee: Huanggang Normal University, Huanggang, Hubei (CN)

( * ) Notice: Subject to any disclaimer, the term of this patent is extended or adjusted under 35 U.S.C. 154(b) by 0 days.

(21) Appl. No.: 15/396,435

(22) Filed: Dec. 31, 2016

(51) Int. Cl.
*A61K 31/335* (2006.01)
*A61K 31/35* (2006.01)
*A61K 31/337* (2006.01)

(52) U.S. Cl.
CPC ............ *A61K 31/337* (2013.01); *A61K 31/35* (2013.01)

(58) Field of Classification Search
CPC .............................. A61K 31/337; A61K 31/35
USPC .................................................. 514/449, 456
See application file for complete search history.

(56) References Cited

U.S. PATENT DOCUMENTS

| | | | | |
|---|---|---|---|---|
| 2002/0016358 A1* | 2/2002 | Ishida | ..................... | A61K 8/498 514/456 |
| 2004/0214882 A1* | 10/2004 | Guthrie | ................... | A61K 31/35 514/456 |
| 2007/0275106 A1* | 11/2007 | Ho | ........................ | A61K 31/352 424/736 |
| 2012/0070502 A1* | 3/2012 | Desai | .................... | A61K 31/337 424/491 |
| 2016/0151298 A1* | 6/2016 | Wright | ................. | A61K 9/5153 424/501 |
| 2017/0042855 A1* | 2/2017 | Summa | ................. | A61K 9/5146 |

* cited by examiner

*Primary Examiner* — Raymond Henley, III
(74) *Attorney, Agent, or Firm* — Bin Lu

(57) ABSTRACT

Disclosed is a method of treating a subject having non-small cell lung cancer. The method includes administering to the subject a therapeutically effective amount of a composition and the composition contains 5-demethylnobiletin and docetaxel. Compared with the use of docetaxel alone, the method of combining 5-demethylnobiletin and docetaxel had a 4.4 fold increase in inhibiting the growth of human lung cancer cells, and had a 3.05 fold increase in inhibiting tumor growth in human lung cancer cell-engrafted nude mice.

12 Claims, 5 Drawing Sheets

COMBINATION THERAPY FOR TREATING CANCER

FIELD OF THE INVENTION

The invention relates to a method for use in the treatment of non-small cell lung cancer in human and animal subjects. More specifically, the present invention provides a combination therapy of using demethylated polymethoxyflavone or polymethoxyflavone in combination with taxane.

BACKGROUND OF THE INVENTION

Lung cancer is one of the most common types of human cancers. Among lung cancer patients, non-small cell lung cancer (NSCLC) accounts for 80-85% of the cancer population. Due to its high malignancy and rapid tumor development, non-small cell lung cancer when discovered and diagnosed, typically in 30-40% patient cases, has already developed into an advanced stage and missed the optimal time for surgical treatment. For those types of the patients, chemotherapy becomes all but the only option to manage the disease.

Taxane is a class of antitumor drugs widely used for chemotherapy. Docetaxel, a member of taxane, binds to intracellular free tubulin and promote the assembly of free tubulin to form stable polymeric microtubules. At the same time, docetaxel can inhibit the polymerization of microtubules depolymerization, thus breaking the dynamic equilibrium between polymerization and depolymerization of the intracellular microtubule of. Because docetaxel can inhibit cell mitosis by impacting spindle formation during mitosis, cells treated with docetaxel cannot divide and proliferate normally. Docetaxel is a semi-synthetic analogue of paclitaxel. Compared with paclitaxel, docetaxel has a higher antitumor activity and has been widely used as a first-line or second-line treatment for non-small cell lung cancer (Lin et al., China Cancer, 2008, 17(4):326-327. doi: 10.3969/j.issn.1004-0242.2008.04.019). However, the current clinical use of chemotherapy drugs including docetaxel for non-small cell lung cancer suffers from low efficiency. According to Cancer statistics (Siegel R L, Miller K D, Jemal A. CA Cancer J Clin. 2015, 65(1):5-29. doi: 10.3322/caac.21254), only 20-30% of patients responded, while non-small cell lung cancer is seen prone to metastasis and easy to relapse in treated patients.

Clearly, there is an urgent need to develop an effective therapy for non-small cell lung cancer as the current clinical application of chemotherapy drugs has not met the needs for treatment.

In recent years, it has been confirmed by a number of studies that natural substances extracted from plants have strong anti-tumor activities. It has been reported that nobiletin (5,6,7,8,3',4'-hexamethoxyflavone) can block the cell cycle in the G1 phase and the cell apoptosis (Qiu P, Dong P, Guan H, Li S, Ho C T, Pan M H, McClements D J, Xiao H. Inhibitory effects of 5-hydroxy polymethoxyflavones on colon cancer cells. Mol Nutr Food Res. 2010, Suppl 2:S244-52. doi: 10.1002/mnfr.200900605).

It is thus of high utility to explore nobiletin, its analogs, or its derivatives for treating cancer including non-small cell lung cancer.

SUMMARY OF THE INVENTION

This invention provides a combination therapy of using phytochemicals and taxane to treat non-small cell lung cancer. Using a naturally derived agent, the method described below provides a safe and effective way to manage the otherwise difficult disease.

One aspect of this invention relates to a method of treating a subject having non-small cell lung cancer. The method includes administering to the subject an effective amount of a composition and the composition contains demethylated polymethoxyflavone or polymethoxyflavone and taxane.

Typically, the demethylated polymethoxyflavone described above can be 5-demethylpolymethoxyflavone. More specifically, the demethylated polymethoxyflavone can be 5-demethylhesperetin, 5-demethylnobiletin, 5-demethylsinensetin, 5-hydroxy-3,6,7,8,3',4'-hexamethoxyflavone, 5-hydroxy-3,6,7,3',4'-pentamethoxyflavone, 5-hydroxy-6,7,4'-triamethoxyflavone, 7-demethylpolymethoxyflavone, 6-demethylpolymethoxyflavone, 8-demethylpolymethoxyflavone, 3'-demethylpolymethoxyflavone, 4'-demethylpolymethoxyflavone, 3-demethylpolymethoxyflavone, 3',4'-bis-demethylpolymethoxyflavone, 5,4'-bis-demethylpolymethoxyflavone, or a combination thereof.

Examples of the polymethoxyflavone described above include hesperetin, nobiletin, 3,5,6,7,8,3',4'-heptamethoxyflavone, sinensetin, 3,5,6,7,3',4'-hexamethoxyflavone, 5,6,7,4'-tetramethoxyflavone, 3,5,6,3',4'-pentamethoxyflavone, or a combination thereof. On the other hand, examples of the taxane include paclitaxel, docetaxel, or a combination thereof.

Preferably, the composition contains 5-demethylnobiletin and docetaxel.

The 5-demethylnobiletin can be administered in an amount of 6.3 µmol/L-15.5 µmol/L and one example of the amount of the 5-demethylnobiletin is 10 µmol/L.

The docetaxel, on the other hand, can be administered in an amount of 3.125 nmol/L-25 µmol/L and one example of the amount of the docetaxel is 6.7 µmol/L Another aspect of this invention relates to a method of inhibiting lung cancer cells. The method includes contacting the lung cancer cells with a therapeutically effective amount of a composition and the composition contains demethylated polymethoxyflavone or polymethoxyflavone and taxane. Examples of the demethylated polymethoxyflavone, polymethoxyflavone, and taxane are enumerated above. Preferably, the composition contains 5-demethylnobiletin and docetaxel. Examples of the lung cancer cells include human lung cancer cell CL1-5 and transplanted human lung cancer cell CL1-5 in a laboratory animal. The laboratory animal can be a BALB/c nude mouse.

The details of the invention are set forth in the drawing and description below. Other features, objects, and advantages of the invention will be apparent from the description and from the claims.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
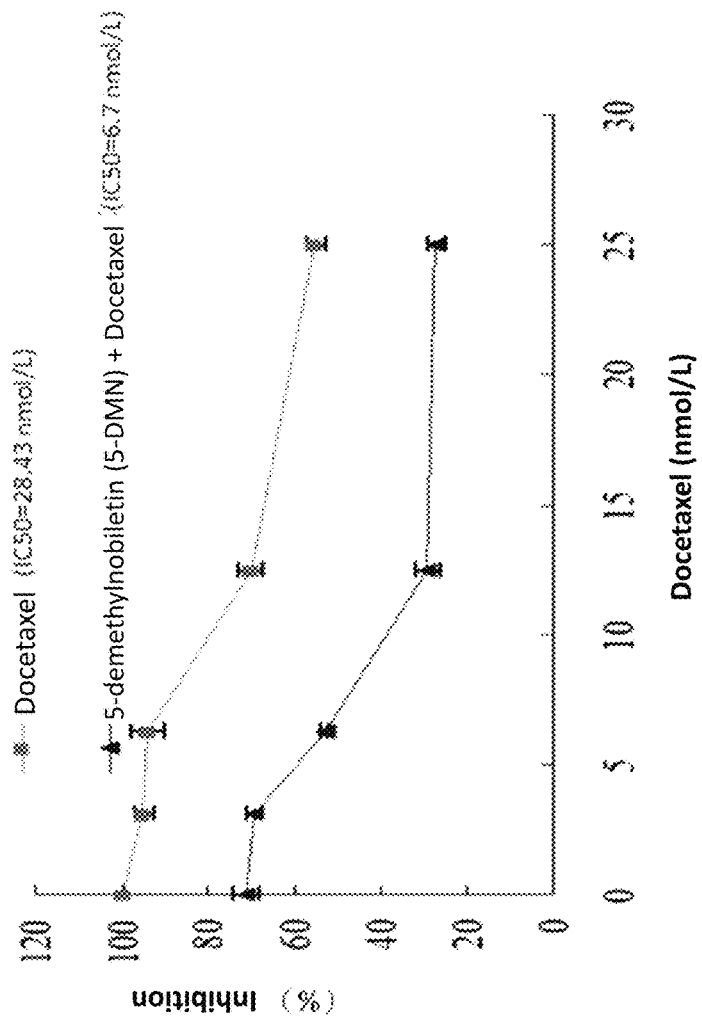
FIG. 1 is a diagram illustrating growth inhibition by combining 5-demethylnobiletin (5-DMN) and docetaxel in CL1-5 lung cancer cells.

Many non-small cell lung cancer patients were diagnosed at the late stage of the disease, when the optimal time for surgery has passed. Radiotherapy or chemotherapy thus becomes the only option of treatment. However, the outcome of non-small cell lung cancer from either radiotherapy or chemotherapy remains poor, with cancer often relapsing or metastasizing. The method of the present invention provides a combination therapy to treat non-small cell lung cancer by using demethylated polymethoxyflavone or polymethoxyflavone and taxane, and more specifically, by using 5-demethylnobiletin and docetaxel. This combination therapy has been shown by studies in cell lines and animal models to be more effective in treating cancer than the monotherapy of docetaxel. Compared with the use of docetaxel alone, it required less docetaxel, showed fewer side effects of chemotherapy, and lowers the overall treatment costs.

The demethylated polymethoxyflavone used in the method of the present invention can be a flavone substituted by two or more of methoxyl and by one or more of hydroxyl. Examples include 5-demethylhesperetin, 5-demethylnobiletin, 5-demethylsinensetin, 5-hydroxy-3,6,7,8,3',4'-hexamethoxyflavone, 5-hydroxy-3,6,7,3',4'-pentamethoxyflavone, 5-hydroxy-6,7,4'-triamethoxyflavone, 7-demethylpolymethoxyflavone, 6-demethylpolymethoxyflavone, 8-demethylpolymethoxyflavone, 3'-demethylpolymethoxyflavone, 4'-demethylpolymethoxyflavone, 3-demethylpolymethoxyflavone, 3',4'-bis-demethylpolymethoxyflavone, 5,4'-bis-demethylpolymethoxyflavone, and an analog thereof.

The polymethoxyflavone used can be a flavone substituted by two or more of methoxyl. Examples include hesperetin, nobiletin, 3,5,6,7,8,3',4'-heptamethoxyflavone, sinensetin, 3,5,6,7,3',4'-hexamethoxyflavone, 5,6,7,4'-tetramethoxyflavone, 3,5,6,3',4'-pentamethoxyflavone, and an analog thereof.

5-demethylnobiletin (IUPAC name: 5-Hydroxy-6,7,8,3',4'-pentamethoxyflavone or 2-(3,4-dimethoxyphenyl)-5-hydroxy-6,7,8-trimethoxychromen-4-one, CAS number: 2174-59-6) is one of the most abundant 5-demethylated polymethoxyflavones found in orange peel, and it can be formed via auto-hydrolysis of nobiletin during long-term storage. The 5-demethylnobiletin used was prepared by dissolving in 10% DMSO.

The Taxane used in the method of the present invention includes docetaxel (IUPAC name: 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and paclitaxel (Taxol, IUPAC name: (2α,4α,5β,7β,10β,13α)-4,10-Bis(acetyloxy)-13-{[(2R,3 S)-3-(benzoylamino)-2-hydroxy-3-phenylpropanoyl]oxy}-1,7-dihydroxy-9-oxo-5,20-epoxytax-11-en-2-yl benzoate). The docetaxel used was prepared by dissolving in 10% DMSO.

The method of the present invention has been shown to inhibit the growth of lung cancer cells. The study was conducted using human lung cancer cell line CL1-5 as follows: culturing the cell line in RPMI 1640 medium; adding docetaxel with varying concentrations (3.125, 6.25, 12.5, and 25.0 nmol per liter of the medium in 100 µl of 10% DMSO solution) with or without 5-demethylnobiletin (10 µmol per liter of the medium); collecting the treated cells after 48 hs of culturing and determining the cell viability by measuring light absorbance of the cells; and calculating the $IC_{50}$ rate of docetaxel for the CL1-5 cells.

Results obtained from the study showed that the growth inhibition of CL1-5 cells by combining 5-demethylnobiletin and docetaxel had a 4.4 fold increase as compared with the use of docetaxel alone.

Further, the instant method has been shown to inhibit the tumor growth in CL1-5 cell-engrafted BALB/c nude mice. The study was carried out as follows: inoculating BALB/c mice with of the CL1-5 human lung cancer cells; dividing the mice into 4 groups 7 days after inoculation with 8 mice in each group and treating them once every two days for 14 days respectively with (i) 0.4 ml of 10% DMSO, (ii) 0.4 ml of 10% DMSO containing 25 µmol of docetaxel, (iii) 0.4 ml of 10% DMSO containing 15.5 µmol of 5-demethylnobiletin, and (iv) 0.4 ml of 10% DMSO containing 25 µmol of docetaxel and 15.5 µmol of 5-demethylnobiletin; growing mice without any treatment for another 14 days; measuring tumor sizes after animal sacrificing.

Results obtained from the study exhibited that the combination therapy had a 3.05 fold increase in inhibiting tumor growth in human cancer cell-engrafted nude mice as compared with the use of docetaxel alone.

Examples

Example 1: Effects of Combining 5-Demethylnobiletin and Docetaxel in CL1-5 Lung Cancer Cells Growth Inhibition The CL1-5 cells were cultured in RPMI 1640 medium containing 100 U/ml penicillin, 100 µg/ml streptomycin, and 10% fetal bovine serum at a temperature of 37° C. and with carbon dioxide at a concentration of 5%. The cultured cells were divided into 8 treatment groups. 4 groups were treated only with docetaxel at different concentrations: 3.125, 6.25, 12.5, and 25.0 nmol of docetaxel per liter of the medium in 100 µl of 10% DMSO solution. The other 4 groups were treated with docetaxel in the same manner except that 10 µmol of 5-demethylnobiletin per liter of the medium was added to the each group.

After culturing for 48 hs, the cells were collected and the absorbance of each treatment group was measured for calculating the $IC_{50}$ rate of docetaxel for the CL1-5 cells (FIG. 1). The results show that, when the CL1-5 cells were treated only with docetaxel, the $IC_{50}$ rate is 28.43 nmol/L. However, when the CL1-5 cells were treated combinatorially with 5-demethylnobiletin and docetaxel, the $IC_{50}$ rate is 6.7 nmol/L, unexpectedly much lower.

Cell Cycle and Apoptosis

To further elucidate the mechanism of growth inhibition of the CL1-5 human lung cancer cells by the combined 5-demethylnobiletin and docetaxel, a comparative study was conducted on treatment with 5-demethylnobiletin, docetaxel, or 5-demethylnobiletin combined with docetaxel. Specifically, cultured CL1-5 cells were divided into 4 groups and, except the control group, the 3 other groups were treated respectively with: (i) 6.3 µmol of 5-demethylnobiletin per liter of the medium; (ii) 10 nmol of docetaxel per liter of the medium; and (iii) combined treatments (i) and (ii). All treatment drugs were prepared in a 10% DMSO solution.

The treated cells were incubated for 24 hs before collected in a centrifuge tube. The cells were then washed with PBS at 4° C. and n mixed with 70% ethanol pre-cooled at −20° C. before kept at 4° C. overnight. Next, the cells were centrifuged at 1000 rpm to remove ethanol and the cell density was adjusted to $(1-2)\times 10^6$ cells/ml by add PBS. Following adding PI and DNase-free RNase to respectively reach final concentrations of 50 μg/ml and 50 g/ml, the cells were stained for cell cycle and apoptosis studies by flow cytometry. All studies were repeated 3 times and the averages were calculated.

Figure 2:
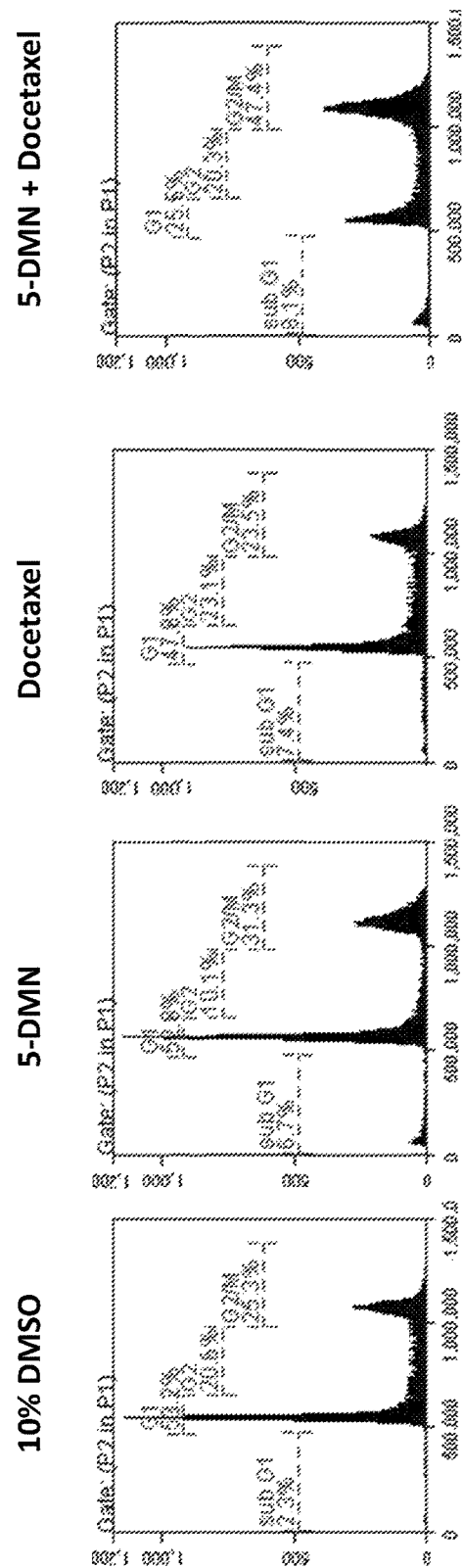
FIG. 2 is a bar diagram that shows effect of cell cycle distribution by combining 5-demethylnobiletin and docetaxel in CL1-5 lung cancer cells.

The results show that either 5-demethylnobiletin or docetaxel promoted the G2/M phase accumulation for the treated cancer cells. Specifically, G2/M phase cells accounted for 31.3% and 23.5% of the total cells treated with 5-demethylnobiletin and docetaxel, respectively. Yet, the number of cells in the G2/M phase increased significantly when the cancer cells were treated combinatorially with 5-demethylnobiletin and docetaxel and accounted for 47.4% of all cells (FIG. 2).

Figure 3:
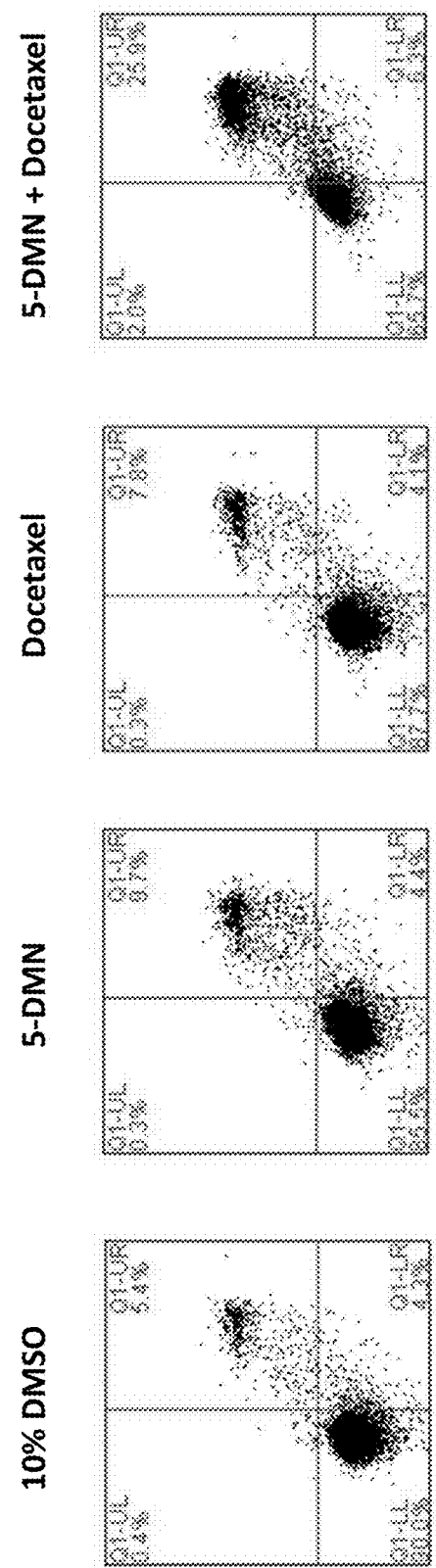
FIG. 3 is a diagram showing effect on apoptosis by combining 5-demethylnobiletin and docetaxel in CL1-5 lung cancer cells.

The results also show that the percentage of apoptotic cells in the control, 5-demethylnobiletin-treated and docetaxel-treated groups were 5.4%, 9.7%, 7.8%, respectively. However, unexpectedly, that percentage in the combinatorially treated group was 25.9%, which was much greater (FIG. 3). The results demonstrate that the combination regimen could induce much more G2/M arrest in the lung cancer cells and lead to their apoptosis much more effectively.

Figure 4:
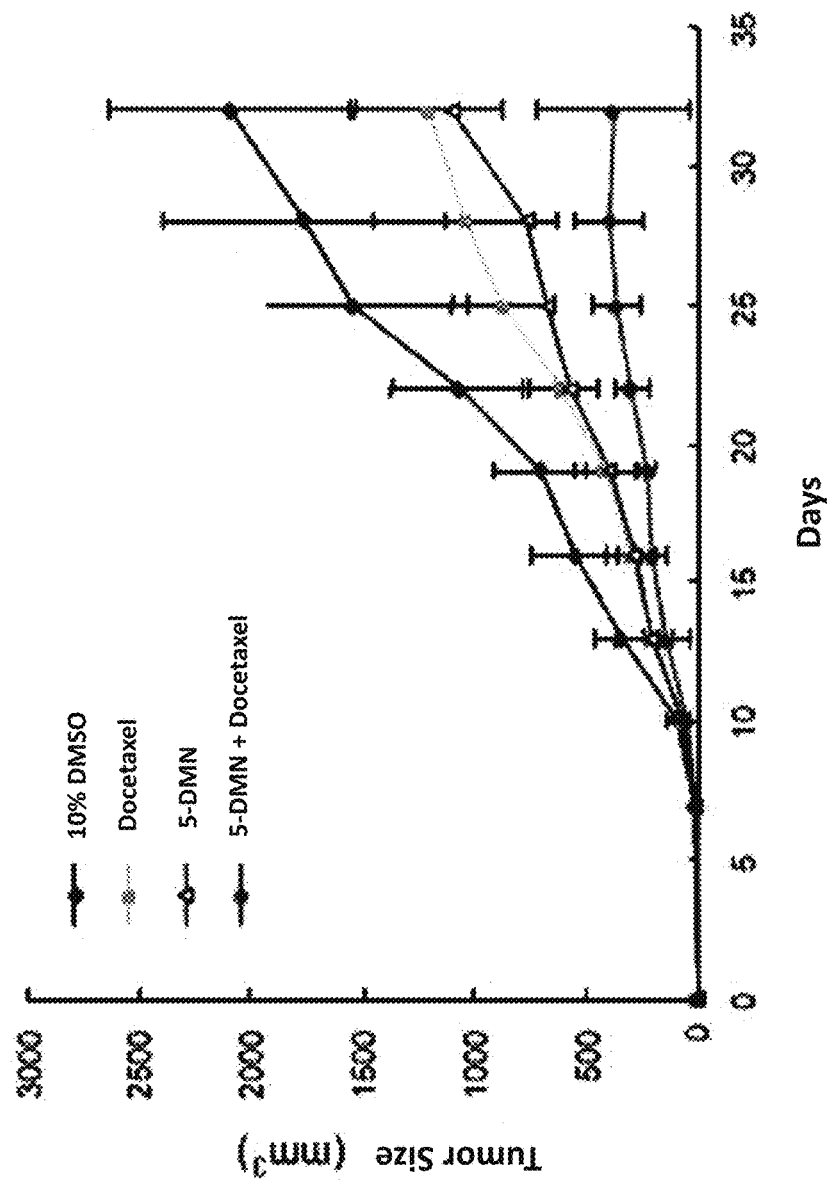
FIG. 4 is a plot showing 5-demethylnobiletin and docetaxel inhibiting tumor growth in human cancer cell-engrafted nude mice.
Figure 5:
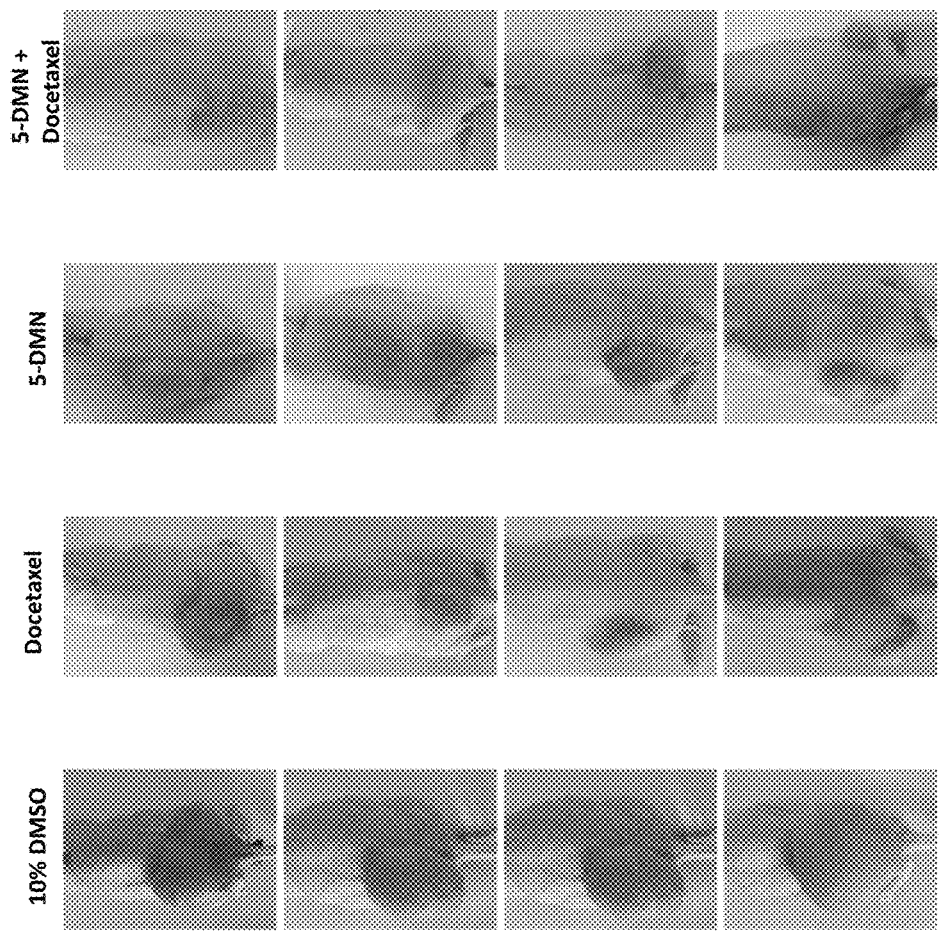
FIG. 5 is a diagram showing 5-demethylnobiletin and docetaxel inhibiting tumor growth in human cancer cell-engrafted nude mice.

Example 2: Effects of Combining 5-Demethylnobiletin and Docetaxel on Tumor Growth in CL1-5 Cell-Engrafted BALB/c Nude Mice The experimental BALB/c nude mice were divided into 4 groups, with 8 in each group. Each mouse was inoculated with 0.1 ml of the CL1-5 human lung cancer cells at a density of $10^6$ cells/ml. 7 days after of the inoculation, the 4 groups of mice were infused respectively with (i) 27 μl of 10% DMSO; (ii) 25 μmol of docetaxel in a 10% DMSO solution (iii) 15.5 μmol of 5-demethylnobiletin in a 10% DMSO solution; and (iv) 25 μmol of docetaxel and 15.5 μmol of 5-demethylnobiletin in a 10% DMSO solution at a frequency of once every 2 days for 14 days. The mice were sacrificed after another 14 days without any treatment. Finally, sizes of tumors in each group of mice were measured and their averages were calculated (FIGS. 4 and 5).

The results show that while the average tumor in the docetaxel-treated group had a size of 1230 mm³, that in the combinatorially treated group had an unexpectedly low size, i.e., only 403 mm³.

The synergistic effect of the combination of 5-demethylnobiletin and docetaxel could be calculated according to the Webb's fractional product method as follows: $(fa)_{1,2}=1-[1-(fa)_1][1-(fa)_2]$, $(fa)_1$ and $(fa)_2$ are inhibition rates of drug1 and drug2, respectively, and $(fa)_{1,2}$ is the calculated inhibition rate of combining drug1 and drug2, which is also a theoretical additive effect. If the experimental inhibition rate of combining drug1 and drug2 is greater than the theoretical additive effect, a synergy between drug1 and drug2 is evident.

In this experiment, $(fa)_1=38\%$, $(fa)_2=47.6\%$, then, $(fa)_{1,2}=1-(1-0.38)(1-0.476)=0.675=67.5\%$. Yet, according to the results of the experiment, the experimental inhibition rate of combining 5-demethylnobiletin and docetaxel is 80.9%, much greater than 67.5%, the theoretical additive effect, indicating that 5-demethylnobiletin and docetaxel in combination had a synergistic effect.

Example 3: Evaluation of Toxicity of 5-Demethylnobiletin on BALB/c Nude Mice It is imperative to ensure that applying 5-demethylnobiletin in vivo does not present any safety concern. BALB/c nude mice were divided into two groups, with 8 mice in each group. The first group of mice was a control group, given daily laboratory rodents feed, plus fed with 0.4 mL of 10% DMSO; the second group was 5-demethylnobiletin treatment group. After the study started, the second group of mice was fed with a 0.4 mL 10% DMSO solution containing 15.5 μmol 5-demethylnobiletin at a frequency of once every 2 days for 14 days. The mice were sacrificed after another 14 days without any treatment. Then, liver, spleen, and kidney weights of the mice in each group were measured and blood was collected. Following at RT for 1 h, the blood was centrifuged at 3000 rpm for 10 min at 4° C. to collect serum before stored at −80° C. Clinical chemistry measurements, e.g., levels of AST, ALT, triglyceride (TG), and total cholesterol (TC), were measured by an automatic biochemical analyzer. The experimental results are shown in Table 1. The results show that there is no significant difference between the control group and the 5-demethylnobiletin treatment group, indicating that 5-demethylnobiletin has a good in vivo safety profile.

TABLE 1

Evaluation of toxicity of 5-demethylnobiletin on BALB/c nude mice

| Study Group | Liver (g) | Kidney (g) | Spleen (g) | GOT (Unit/L) | GPT (Unit/L) | TG (mg/dl) | TC (mg/dl) |
|---|---|---|---|---|---|---|---|
| BALB/c nude control | 3.89 ± 0.35 | 0.88 ± 0.09 | 0.23 ± 0.02 | 90.3 ± 10.5 | 21.5 ± 5.3 | 107.4 ± 35.2 | 75.9 ± 5.8 |
| 5-demethylnobiletin treatment group | 3.93 ± 0.28 | 0.90 ± 0.06 | 0.21 ± 0.04 | 91.2 ± 9.8 | 22.8 ± 5.2 | 109.5 ± 36.9 | 77.1 ± 4.9 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a subject having non-small cell lung cancer, the method comprising administering to the subject a therapeutically effective amount of a composition, wherein the composition comprises demethylated polymethoxyflavone or polymethoxyflavone and taxane.

2. The method of claim 1, wherein the demethylated polymethoxyflavone is 5-demethylpolymethoxyflavone.

3. The method of claim 1, wherein the demethylated polymethoxyflavone is 5-demethylhesperetin, 5-demethylnobiletin, 5-demethylsinensetin, 5-hydroxy-3,6,7,8,3',4'-hexamethoxyflavone, 5-hydroxy-3,6,7,3',4'-pentamethoxyflavone, 5-hydroxy-6,7,4'-triamethoxyflavone, 7-demethylpolymethoxyflavone, 6-demethylpolymethoxyflavone, 8-demethylpolymethoxyflavone, 3'-demethylpolymethoxyflavone, 4'-demethylpolymethoxyflavone, 3-demethylpolymethoxyflavone, 3',4'-bis-demethylpolymethoxyflavone, 5,4'-bis-demethylpolymethoxyflavone, or a combination thereof.

4. The method of claim 1, wherein the polymethoxyflavone is hesperetin, nobiletin, 3,5,6,7,8,3',4'-heptamethoxyflavone, sinensetin, 3,5,6,7,3',4'-hexamethoxyflavone, 5,6,7,4'-tetramethoxyflavone, 3,5,6,3',4'-pentamethoxyflavone, or a combination thereof.

5. The method of claim 1, wherein the taxane is paclitaxel, docetaxel, or a combination thereof.

6. The method of claim 1, wherein the composition comprises 5-demethylnobiletin and docetaxel.

7. The method of claim 6, wherein the 5-demethylnobiletin is administered in an amount of 6.3 μmol/L-15.5 μmol/L and the docetaxel is administered in an amount of 3.125 nmol/L-25 μmol/L.

8. The method of claim 7, wherein the 5-demethylnobiletin is administered in an amount of 10 μmol/L and the docetaxel is administered in an amount of 6.7 μmol/L.

9. A method of inhibiting lung cancer cells, the method comprising contacting the lung cancer cells with a therapeutically effective amount of a composition, wherein the composition comprises demethylated polymethoxyflavone or polymethoxyflavone and taxane.

10. The method of claim 9, wherein the composition comprises 5-demethylnobiletin and docetaxel.

11. The method of claim 10, wherein the lung cancer cells comprises human lung cancer cell CL1-5.

12. The method of claim 10, wherein the lung cancer cells comprises transplanted human lung cancer cell CL1-5 in a laboratory animal, wherein the laboratory animal is a BALB/c nude mouse.

* * * * *